(12) United States Patent
Moore

(10) Patent No.: US 10,188,842 B2
(45) Date of Patent: Jan. 29, 2019

(54) APPARATUS AND METHOD FOR DEPLOYING A SURGICAL PREPARATION

(71) Applicant: Mark R. Moore, Westlake, LA (US)

(72) Inventor: Mark R. Moore, Westlake, LA (US)

( * ) Notice: Subject to any disclaimer, the term of this patent is extended or adjusted under 35 U.S.C. 154(b) by 430 days.

(21) Appl. No.: 15/005,750

(22) Filed: Jan. 25, 2016

(65) Prior Publication Data

US 2016/0136404 A1    May 19, 2016

Related U.S. Application Data

(63) Continuation-in-part of application No. 14/312,498, filed on Jun. 23, 2014, now Pat. No. 9,409,005, which is a continuation-in-part of application No. 13/199,343, filed on Aug. 26, 2011, now Pat. No. 8,758,310, which is a continuation-in-part of application No. 11/602,542, filed on Nov. 21, 2006, now Pat. No. 8,403,898.

(51) Int. Cl.
| | |
|---|---|
| *A61B 90/40* | (2016.01) |
| *A61B 90/80* | (2016.01) |
| *A61F 15/00* | (2006.01) |
| *A61H 33/00* | (2006.01) |
| *A61M 35/00* | (2006.01) |
| *A61H 35/00* | (2006.01) |
| *A61F 13/02* | (2006.01) |

(52) U.S. Cl.
CPC ............. *A61M 35/00* (2013.01); *A61B 90/40* (2016.02); *A61B 90/80* (2016.02); *A61F 13/02* (2013.01); *A61F 15/004* (2013.01); *A61F 15/008* (2013.01); *A61H 33/00* (2013.01); *A61H 35/00* (2013.01); *A61H 35/006* (2013.01); *A61H 2201/0103* (2013.01); *A61H 2201/0111* (2013.01); *A61H 2201/1692* (2013.01); *A61H 2205/06* (2013.01); *A61H 2205/065* (2013.01); *A61H 2205/10* (2013.01); *A61H 2205/106* (2013.01); *A61M 2205/0205* (2013.01); *A61M 2210/083* (2013.01); *A61M 2210/086* (2013.01)

(58) Field of Classification Search
CPC .............. A61F 2007/022; A61F 15/004; A61F 15/008; A61F 15/0082; A61M 35/00; A61B 90/40; A61B 90/80; A61H 33/00; A61H 35/00; A61H 35/006; A61H 2201/1692; A61H 2205/06; A61H 2205/065; A61H 2205/10; A61H 2205/106
See application file for complete search history.

(56) References Cited

U.S. PATENT DOCUMENTS

| | | |
|---|---|---|
| 871,689 A | 11/1907 | Ganzhorn |
| 2,690,747 A | 10/1954 | Frallic |
| (Continued) | | |

*Primary Examiner* — Lynne Anderson
(74) *Attorney, Agent, or Firm* — Schultz & Associates, P.C.

(57) ABSTRACT

A device used for applying an antiseptic preparation to a surgical site of a patient prior to surgery outside of an operating theater. A loose-fitting bag is provided which encloses the surgical site by securing the open end(s) to the patient by closing means. A high friction scrub surface is provided in the bag. A method and apparatus are also provided for releasing antiseptic into the interior of the bag. The method provides that the surgical site can be scrubbed within the bag so as to properly prepare the skin for surgery. A temperature indicator for the antiseptic preparation is also provided.

19 Claims, 11 Drawing Sheets

(56) References Cited

U.S. PATENT DOCUMENTS

| | | | |
|---|---|---|---|
| 3,327,705 A | 6/1967 | Spira et al. | |
| 4,808,172 A | 2/1989 | Murata | |
| 4,858,604 A | 8/1989 | Konishi | |
| 5,312,385 A | 5/1994 | Greco | |
| 5,447,504 A | 9/1995 | Baker | |
| 5,592,953 A | 1/1997 | Delao | |
| 5,609,163 A | 3/1997 | Beard | |
| 5,702,356 A | 12/1997 | Hathman | |
| 5,769,806 A | 6/1998 | Radow | |
| 5,823,977 A | 10/1998 | Dalyea | |
| 5,848,998 A | 12/1998 | Marasco | |
| 6,007,564 A | 12/1999 | Haverstock | |
| 6,083,209 A | 7/2000 | Marasco | |
| 6,241,697 B1 | 6/2001 | Augustine | |
| 6,450,982 B1 | 9/2002 | Peterson | |
| 6,635,035 B1 | 10/2003 | Marasco | |
| 6,664,434 B2 | 12/2003 | Cominsky | |
| 6,992,233 B2 | 1/2006 | Drake et al. | |
| 8,048,044 B2 | 11/2011 | Stryker | |
| 8,206,363 B2 | 6/2012 | Bainbridge | |
| 8,298,197 B2 | 10/2012 | Eriksson | |
| 8,353,882 B1 | 1/2013 | Pelkus | |
| 8,403,898 B2 | 3/2013 | Moore | |
| 8,603,150 B2 * | 12/2013 | Kane | A61F 7/007 607/111 |
| 2004/0171998 A1 | 9/2004 | Marasco | |
| 2012/0246820 A1 | 10/2012 | Huynh | |
| 2015/0119772 A1 * | 4/2015 | Ruetenik | A01K 13/007 601/149 |

* cited by examiner

APPARATUS AND METHOD FOR DEPLOYING A SURGICAL PREPARATION

CROSS REFERENCE TO RELATED APPLICATION

This application is a continuation in part of application Ser. No. 14/312,498, filed Jun. 23, 2014, which is a continuation in part of application Ser. No. 13/199,343 filed Aug. 26, 2011, now U.S. Pat. No. 8,758,310, which is a continuation in part of application Ser. No. 11/602,542 filed Nov. 21, 2006, now U.S. Pat. No. 8,403,898.

FIELD OF THE INVENTION

This present invention relates to a method to an apparatus and method for applying antiseptic prior to surgery.

BACKGROUND OF THE INVENTION

Surgical site infections are frequently caused by bacteria commonly found on the surface of the skin. Since 1867, when Joseph Lister discovered the link between microbes and patient mortality after operations, he coined the term "antiseptic" after discovering that certain surgical preparations could be applied before surgery to eliminate bacteria. Practitioners have used aseptic techniques to reduce post-operative infections ever since.

In order to reduce bacteria, antiseptics are used prior to conducting the surgery to clean and disinfect the surgical site. Types of antiseptics include alcohols, iodine or iodine-containing compounds and chlorhexidine gluconate among others. There are two primary types of iodine-containing compounds, tincture of iodine, and iodophors. Tincture of iodine is an alcohol solution and was one of the first antiseptics used. However, iodophors are more commonly used today to prepare a surgical site for surgery.

The most common aseptic technique for sterilizing a surgical site requires application of an antiseptic solution immediately prior to the surgical procedure in the sterile operating theater after the patient has been anesthetized. When performing surgery to the extremities, i.e., leg or arm, the entire extremity is typically cleaned with the antiseptic solution. A sponge is immersed in the antiseptic solution, then applied to an area of the extremity with a scrubbing action and then discarded. A new sponge is immersed into the antiseptic solution and applied to a different area of the extremity. This process is then repeated until the entire area has been scrubbed. The scrubbing action physically dislodges bacterial colonies. Once the scrubbing is completed, another antiseptic solution is reapplied with a sponge in a painting action using a new sponge with each repeated application. After this procedure the surgical personnel must wait at least five to seven minutes before beginning the surgical procedure. The delay is required to allow the antiseptic solution to disinfect the surgical site.

There are several problems with the prior art procedure for disinfecting a surgical site. During the application of the antiseptic solution to the extremity, numerous sponges are required to be used and discarded, thus creating waste that must be handled and properly discarded. There is also a possibility that the surgical site will not be completely covered, thus creating a potential for bacteria and other contaminants remaining during surgery and serving as a potential source for post-surgical infection. The application of the antiseptic solution is prone to splashing and uncontrolled spills. Excess antiseptic solution spills creating a potential safety hazard and a potential for infection.

The prior art procedure for applying the antiseptic solution is also costly and time consuming. Operating theaters are expensive to maintain and operate. The time that the antiseptic solution takes to be effective costs the patient and the hospital a significant amount of money. The delay also slows the throughput of the operating theater, thereby raising the cost of the procedure to the hospital and the operating staff.

The prior art procedure puts the patient at an increased risk of morbidity and mortality by increasing the amount of time the patient is under anesthesia.

The current invention provides a device and method for applying an antiseptic solution to a surgical site prior to surgery, but outside the operating theater thus reducing anesthesia time along with operating room time and cost. The invention also contains the spills and reduces waste. Since the application of the antiseptic can be accomplished outside the operating theater, additional time and care can be used in applying the antiseptic, thereby reducing post-surgical infection.

Various prior art devices and methods have been used in the past to cover a wound, protect a wound site, or apply medicine to a wound site. But none of the prior art has been used to streamline application of a surgical antiseptic prior to surgery.

For example, U.S. Pat. No. 2,661,739 to Caskey discloses a casing which is made from elastic material to fit against an extremity to hold an absorbent material against a wound. The casing is surrounded by a fabric jacket to hold the casing and absorbent material in place and exclude contamination from the environment. However, the casing is only disclosed to be used after a wound has occurred and it does not disclose using the device to pre-treat an area prior to surgery. Additionally, it does not allow for the scrubbing of medicine against the skin through the device.

U.S. Pat. No. 6,992,233 to Drake, et al. discloses a delivery system for a flowable medicine to a wound in a confined area. Flowable medicine is contained in a strip which is adhesively applied to the skin such that the medicine is delivered to the wound. The flowable medicine is released when removable seal is removed. Drake does not disclose using the device for application of medicine prior to a wound occurring or to a large area of the body. It is limited to the area covered by the strip. Drake also does not disclose scrubbing the medicine against the skin through the device.

U.S. Pat. No. 6,664,434 to Cominsky discloses using a sealed bag around a wound to contain bodily fluids. The device includes an absorbent layer to absorb the bodily fluids exuding from a wound. It does not disclose using the bag prior to the wound or introduction of an antiseptic fluid within the bag. It also does not disclose the scrubbing of an antiseptic through the device.

The prior art fails to disclose or suggest a surgical solution application for preparing a patent's skin prior to surgery. Therefore, it is desirable to have a device and method for facilitating application of antiseptic solution in a non-sterile environment.

SUMMARY

A surgical preparation solution applicator is described for preparing a patient's skin for surgery prior to entering the surgical theater. More specifically, a device and method for facilitating application of antiseptic solution to a surgical site in a non-sterile environment is described.

The applicator, in one embodiment, includes a bag which is sealed on three sides and open on a fourth side. A resilient seal gasket is affixed to the open end of the applicator bag. The gasket fits snuggly around the patient's body forming a seal between the interior of the bag and patient's body. An antiseptic solution is then introduced into the application bag through either a port in the application bag, a solution deployment pouch within the application bag or through an opening between the gasket and the patient's body. The gasket prevents the release of the antiseptic until removed.

The solution deployment pouch releases antiseptic into the bag once the gasket is secured. The pouch can take the form of a capsule in ducted communication with the application bag which is filled with the antiseptic solution. Other embodiments include one or more ports and/or one or more solution deployment pouches.

In another embodiment, the applicator bag employs other closing means to seal the open end of the application bag securely against the patient's body. This closing means can include but is not limited to a pressure inflatable cuff, a tourniquet, or a pressure strap fixed with a buckle or Velcro® closure.

In another embodiment, the application bag is open on two ends having a resilient seal gasket fixed at each end. In this embodiment, the patient's body is inserted through the seal gaskets at both open ends of the application bag.

In another embodiment, the application bag is suited well for use on a relatively flat area of the body, such as the back or abdomen. In this embodiment, the open end of the bag is secured to the patient with a disk-like adhesive strip. The adhesive strip temporarily adheres to the patient's body during the procedure and acts as a seal between the patient's body and the interior of the bag. After the adhesive is adhered to the patient's body, the antiseptic solution is released inside the application bag, either through a port or by a solution deployment pouch located inside the application bag.

At all places other than the seal gasket, the application bag is loose-fitting around the patient's body to allow the user to manipulate the bag freely and completely apply antiseptic around the body part being treated without breaking the seal of the gasket.

In the preferred embodiment, the application bag is used to disinfect the surgical site before the patient has undergone use of anesthesia. Because the patient is awake, the temperature of the antiseptic solution may be uncomfortable to the patient and increase surgery anxiety in the patient. For this reason, the invention further provides an inexpensive mechanism to monitor the temperature of the antiseptic solution prior to application to the patient. Matching the temperature of the antiseptic solution to the patient aids in reducing pre-surgery anxiety of the patient and therefore a more efficient application of the antiseptic solution.

In yet another preferred embodiment, sterile sponges or other devices used to apply the antiseptic solution to the body can be contained in sealed pouches secured to the inside of the application bag or inside the antiseptic pouch. When the antiseptic is deployed within the bag, the sterile sponges are used to apply the bag and then discarded with the bag prior to surgery.

After this process has been completed, the application bag contains the antiseptic and prevents outside bacteria and contaminants from contacting the treated area. The application bag is designed to remain in place until the patient is positioned in the operating theater. The application bag is removed immediately prior to surgery.

In another embodiment, the application bag is suited well for use on an extremity, preferably a leg. In this embodiment, the application bag is generally shaped to fit around the extremity. The application bag is secured to the extremity with any of, but not limited to, the aforementioned securing means. The application bag further has a plurality of holes, preferably at the anterior knee area and both sides of the ankle to accommodate the attachment of a scrub brush. The application bag has an antiseptic insertion means that includes, but is not limited to, the aforementioned antiseptic means.

The scrub brush includes a brush and a collapsible handle connected to the brush. The brush includes bristles attached to a scrubbing surface. The brush is attached to the inside surface of the application bag at one of the plurality of holes. The collapsible handle is connected to the brush protruding through the application bag allowing a user to move the scrub brush without the user contacting the patient's skin.

In another embodiment, the application bag is comprised of two releasable halves connected to a resilient seal gasket. In this embodiment, the patient's extremity is inserted through the gasket and positioned upon a first half of the application bag. The second half of the application bag is then aligned with the first half of the application bag. The two halves of the application bag are releasably affixed to each other proximate the perimeter of each half using common in the art means such as releasable adhesive or a resealable zipper connection. An antiseptic solution is then introduced into the application bag through either a port in the application bag, a solution deployment pouch within the application bag or through an opening between the gasket and the patient's body. Removal of the application bag is accomplished by peeling away the first half of the bag from the second half of the bag using a tab extending from either or both halves of the bag.

BRIEF DESCRIPTION OF THE DRAWINGS

In the detailed description of the preferred embodiments presented below, reference is made to the accompanying drawings.

DETAILED DESCRIPTION

Figure 1A:
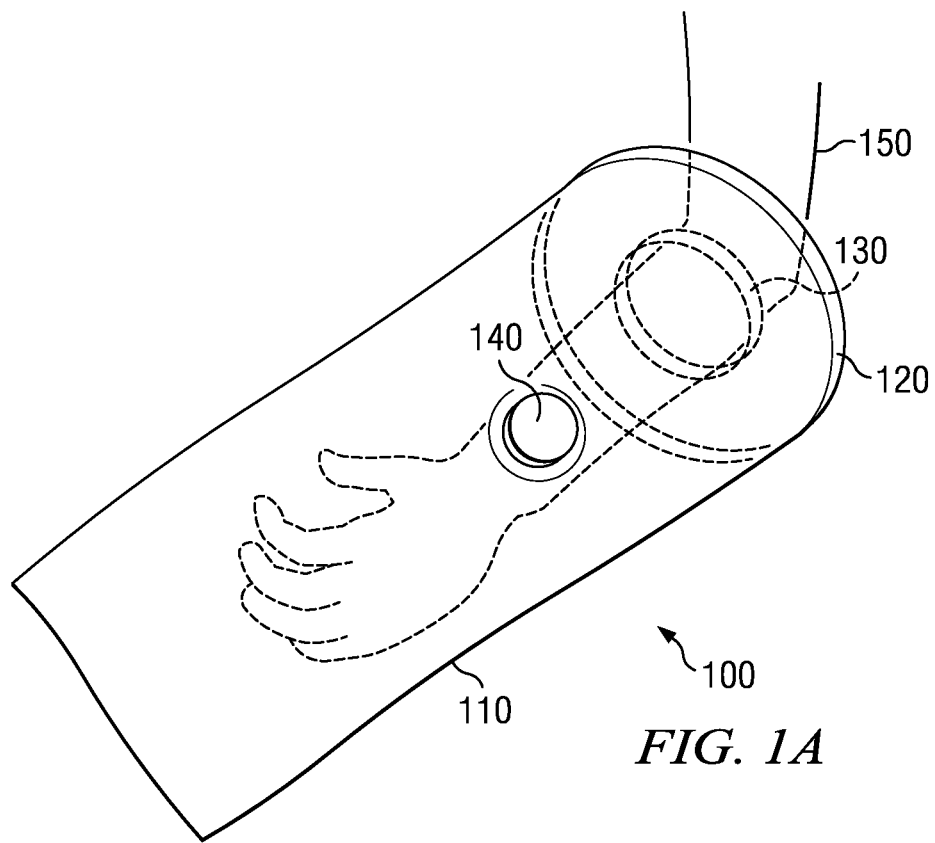
FIG. 1A is a perspective view of an embodiment of the invention showing the use of a flat neoprene gasket seal.

FIG. 1A shows a preferred embodiment of solution applicator 100. Solution applicator 100 includes application bag 110. In the preferred embodiment, application bag 110 is made of HDPE (high density polyethylene) which is typically translucent, but not fully transparent. In other embodiments, the application bag can be made out of LDPE (low density polyethylene) and can be quite clear, but still not totally transparent. In other embodiments, LLDP (linear low density polyethylene) can be employed where a higher structural rigidity is required by the cleaning process. Other flexible sheeting can be used so long as it is inert with respect to the antiseptic solution.

In another preferred embodiment, the interior and/or exterior of the application bag can be textured to increase the effectiveness of the application of the antiseptic to the patient. If on the exterior of the application bag, the purpose of the texturing is to increase friction between the hands of the user and the exterior of the application bag to aid in manipulation of the application bag during use. If on the interior of the application bag, the textured surface is useful in scrubbing the surgical site to remove bacterial colonies. Examples of textures can include raised ribs, chevron patterns, diamond patterns or random "crinkling." Other plastics can be used if complete transparency is required for various cleaning processes. In other embodiments, the application bag can be color coded to indicate different sizes, different antiseptics contained within the bag or the proper operating theater for the patient.

In a preferred embodiment, application bag 110 can be formed from two identical or nearly-identical sized sheets. Both sheets will have the same or nearly the same shape. In a preferred embodiment, the two sheets are rectangular. All of the sides but one are sealed or fused by an adhesive or heat welding as known in the art, leaving the remaining side open. The flat format of the completed application bag increases the ease of storage and/or deployment of the bag from a roll or cardboard box as known in the art. The shape also promotes economy of manufacture.

In another preferred embodiment, application bag 110 can be formed by a flexible tubular extrusion of plastic. After manufacture, the tube can then be cut to length. After being cut, one end is sealed or fused by known inductive welding means leaving the other end open. Other preferred embodiments can include frustroconical shapes, inverted frustroconical shapes and generally spherical shapes.

Different parts of the body can be decontaminated. In FIG. 1A, patient's appendage 150 is shown surrounded by solution applicator 100. The dimensions of the application bag vary depending on the part of the body being decontaminated. Application bag 110 should fit loosely around the body part placed inside application bag 110.

In the preferred embodiment, the general circumference of application bag 110 is at least 2 inches larger than the part of the body being decontaminated. The width of application bag 110 in a preferred embodiment is usually between 2 inches and 40 inches. In the preferred embodiment, the general length of the application bag is at least 2 inches longer than the part of the body being placed in application bag 110. The length of application bag 110 in a preferred embodiment would be between 2 inches and 60 inches. The application bag should also allow for complete articulation of any joint surrounded in order to allow for complete coverage by the antiseptic solution.

Figure 1B:
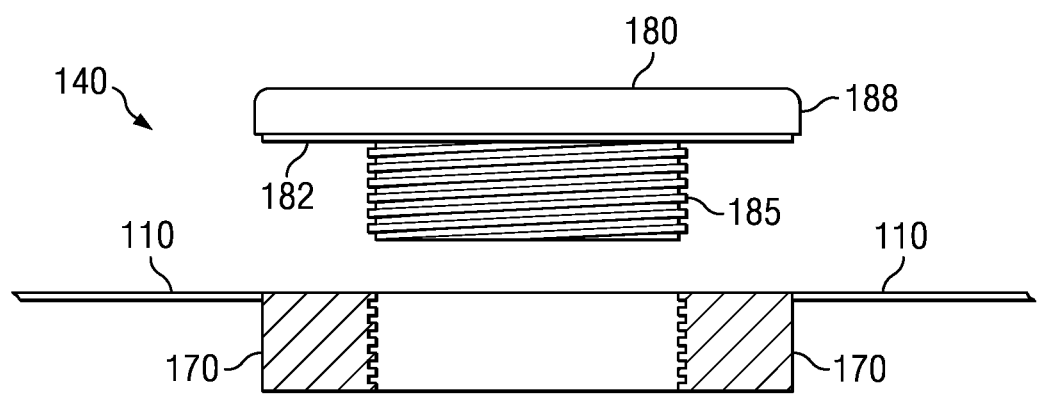
FIG. 1B is a cross sectional view of a preferred embodiment of fill/drain port.

In a preferred embodiment, application bag 110 also includes fill/drain port 140. Fill/drain port 140 allows for deployment of the antiseptic solution into the application bag and draining of excess antiseptic from the application bag. Fill/drain port 140 is located generally in a position to allow for deployment of the antiseptic solution to cover the extremity. FIG. 1B is an expanded view of a preferred embodiment of fill/drain port 140. Fill/drain port 140 includes lid 180. Lid 180 seals opening in application bag 110. Lid 180 includes four parts, cap 188, threaded section 185, flexible gasket 182 and port ring 170. Cap 188 is of such minimum height that it can be easily grasped to open fill/drain port 140. Threaded section 185 width can vary in size between ¼ inch and 4 inches. Threaded section 185 is threaded to match port ring 170.

Port ring 170 is attached to opening in application bag 110 by a known adhesive or heat welding. Port ring 170 is threaded to receive threaded section 185. Port ring 170 is approximately the same depth as the threaded section 185. In the preferred embodiment the depth is between about ¼ of an inch to about 3 inches. A flexible gasket 182 is provided to seal the lid against the port ring. When lid 180 is threaded into port ring 170, bottom of lid 180 fits flush and seals against of port ring 170.

Fill/drain port 140 can be constructed from any commercially available plastic, including but not limited to polypropylene, polyethylene, or polystyrene. In other embodiments, the fill/drain port can be fitted with a quick release mechanism for removal of the antiseptic with a pump through a hose and connection fitting. Other non-threaded resealable cap and base configurations will also suffice.

Attached to open end of application bag 110 is gasket 120. Open end of application bag 110 is affixed to gasket 120 through a known adhesive or heat welding. Gasket 120 can be manufactured from synthetic rubber, such as neoprene, or a resilient plastic polymer. The gasket color can be coded to indicate the size and/or shape of the bag making for easy and error free deployment of the antiseptic solution.

Gasket 120 has hole 130 in the relative center of gasket 120. Patient's appendage 150 is inserted through hole 130 and into application bag 110. In the preferred embodiment, diameter of hole 130 ranges between about 1 inch and 15 inches. However, those skilled in the art will recognize that other sizes can be provided to accommodate different patients and circumstances. Hole 130 should fit around the body extremity such as to prevent the antiseptic solution from escaping application bag 110 when in use.

Figure 2:
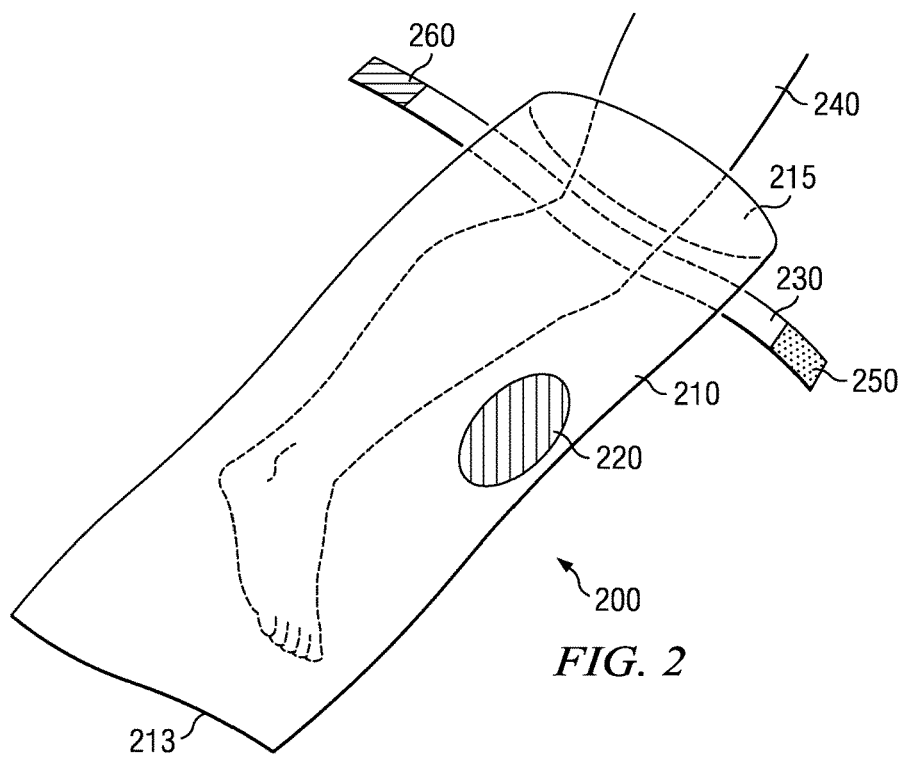
FIG. 2 is a perspective view of a preferred embodiment of the invention showing an alternate closing means.

FIG. 2 shows another preferred embodiment of solution applicator 200. Solution applicator 200 includes application bag 210 which has larger dimensions to accommodate a larger appendage such as a leg. Patient's appendage 240 is inserted into application bag 210 through opening 215 toward closed end 213. This embodiment includes solution deployment pouch 220 and a different closing means.

Application bag 210 is secured around patient's appendage 240 through the use of closing means 230. Some examples of closing means include an elastic band, adhesive tape or strap with a buckle or Velcro® closure. A preferred embodiment includes strap with a Velcro® closure. Closing means 230 allows for securing and sealing application bag 210 around varying size appendages and easy adjustment. Velcro® closure includes hook section 260 and receiver section 250 as necessary to use the closing means 230 as described.

Closing means 230 is located between the opening 215 of application bag 210 and the area to be treated with antiseptic, such that the area to be treated with antiseptic is contained within application bag 210. Closing means 230 can be attached to application bag 210 by commercially available adhesive or can be detachable.

Solution deployment pouch 220 is located on the interior of application bag 210 and contains the antiseptic to be deployed. Solution deployment pouch 220 can vary in size and shape depending on the amount of antiseptic solution contained. In the preferred embodiment, the solution deployment bag contains 2.5 liters of antiseptic solution. The solution deployment pouch may be color coded to indicate the type of antiseptic contained or may be metalized to prevent light from entering the pouch to the detriment of the antiseptic solution. In the preferred embodiment, the antiseptic to be deployed is chlorhexidine, sold under the trademark ChloraPrep® and available from Medi-Flex, Inc. of Leawood, Kans. However, other antiseptics that are effective without evaporation can also be employed.

Figure 3A:
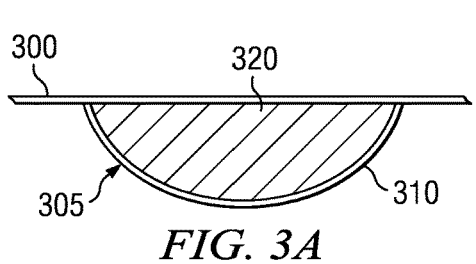
FIG. 3A is cross sectional view of a preferred embodiment of an antiseptic pouch attached to the interior of the application bag.
Figure 3B:
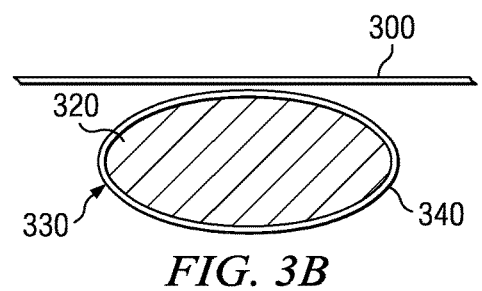
FIG. 3B is a cross sectional view of a preferred embodiment of the invention showing an antiseptic capsule attached to the interior of the application bag.

FIG. 3A and FIG. 3B illustrate two preferred embodiments for solution deployment pouch 220. As shown in FIG. 3A, a cavity 305 is created on the inside of application bag 300 by use of a cavity cover 310. The cavity cover 310 in the preferred embodiment is a hemispherical flexible container heat welded around its circumference to the interior of the application bag. The size of cavity cover 310 will depend on the amount of antiseptic solution 320 to be contained. Cavity cover 310 is of such strength that cavity cover 310 can be ruptured for use but not during normal handling and storage of the application bag. Cavity cover 310 in the preferred embodiment is formed from a 3 ml plastic sheet made of HDPE. When cavity cover 310 is ruptured, antiseptic solution 320 located in the deployment pouch is released to the interior of the application bag.

FIG. 3B shows another preferred embodiment of solution deployment pouch 220. Antiseptic solution 320 is encapsulated in capsule 330. Size and shape of capsule 330 will vary depending on the amount of antiseptic solution 320 contained. Capsule cover 340 forms the outer casing of capsule 330 and encapsulates antiseptic solution 320. Capsule 330, and the encapsulated antiseptic 320, are attached to the inside of application bag 300 by a known adhesive or spot welding. Capsule covering 340 can be manufactured from commercially available plastics. In the preferred embodiment, the covering is HDPE and is about 3 ml thick. In another embodiment, the capsule can be a rigid but fractural plastic capsule contained in a cylindrical form capable of being broken for use through a set of central perforations. Capsule 330 can be attached to application bag 300 at the time of shipment to the user or could be sent separate from the application bag 300 and the user attaches capsule 330 at the time of use.

Multiple capsules or pouches can be used in a single application bag depending on the decontamination method being addressed. Further, differing antiseptic solutions can be contained in different capsules. Furthermore, sterile sponges, brushes and swabs can be contained in the capsule at the time of manufacture for use within the application bag to scrub the surgical site.

Figure 3C:
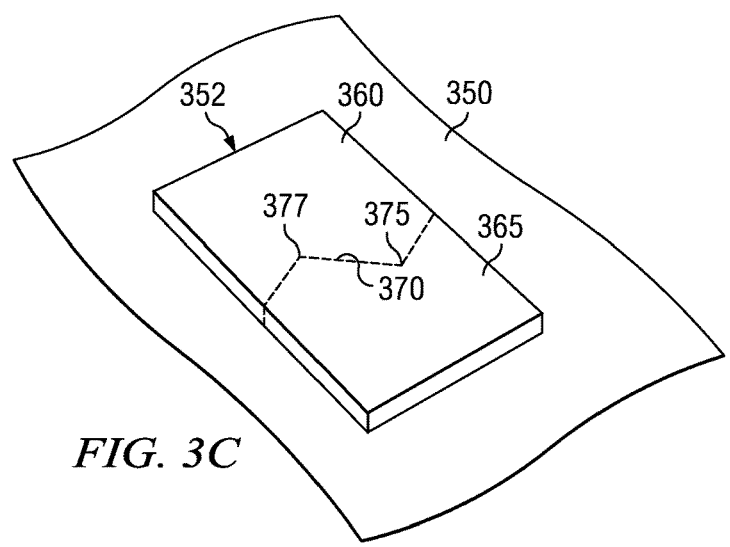
FIG. 3C is a perspective view of a puncturing device used in a preferred embodiment of the invention.

Referring now to FIG. 3C, a puncturing device is shown used in the preferred embodiment of the invention which allows for easy puncturing of the deployment pouch and/or temperature monitoring. The surface of the deployment pouch is shown as 350. Fixed to the external surface of deployment pouch 350 is a rigid plastic rectangle 352. In the preferred embodiment, the dimensions of the plastic rectangle are approximately 10 ml thick and formed of a rigid polystyrene. Other rigid plastics or light metals such as aluminum can be used as well. Plastic rectangle 352 includes halves 360 and 365 separated by a perforation 370. Perforation 370 in the preferred embodiment traverses the rectangle in an angled fashion, including two pointed extensions 375 and 377.

In use, plastic rectangle 352 is broken along perforation 370 separating the two halves 360 and 365. Pointed extensions 377 and 375 are then available to breach the surface of deployment pouch 350 thereby allowing the antiseptic fluid contained to escape into the application bag. The advantage of the use of plastic rectangle 352 is to allow controlled dispersion of the antiseptic fluid and to allow a thicker and more robust flexible plastic to be used for the deployment pouch.

In yet another embodiment, plastic rectangle 352 can include a temperature sensitive dye. The temperature sensitive dye can be used to indicate the temperature of the antiseptic contained in the deployment pouch to allow for an accurate and effective dispensing temperature or for patient comfort.

Figure 4:
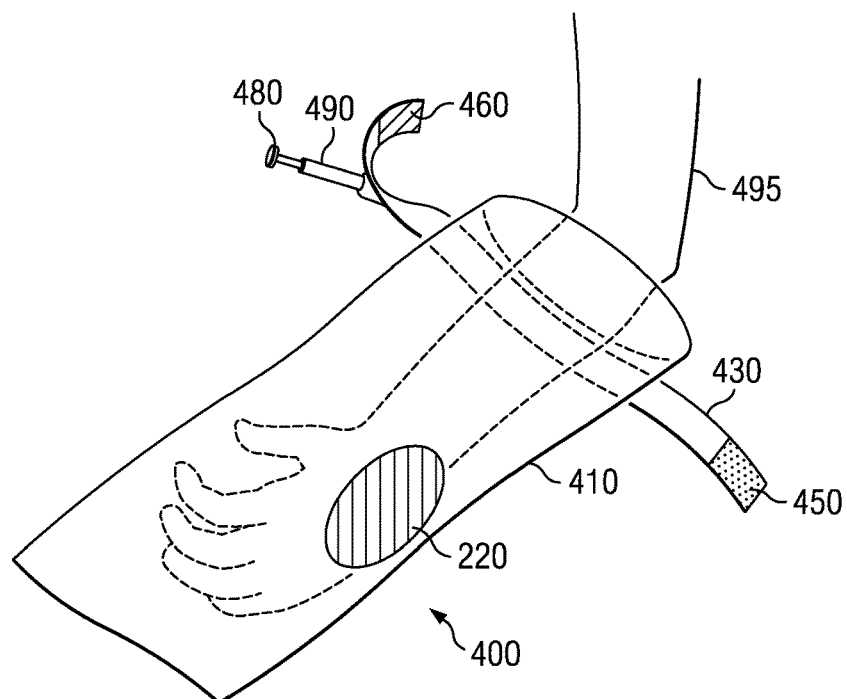
FIG. 4 is a perspective view of a preferred embodiment of the invention showing an alternate closing means.

FIG. 4 shows yet another preferred embodiment of invention. Solution applicator 400 is application bag 410 with one end sealed and one end open. Patient's appendage 495 is placed inside application bag 410 through the open end.

In this embodiment, application bag 410 is closed around patient's appendage 495 by use of pressure inflatable cuff 430. Pressure inflatable cuff 430 can be secured by any appropriate closing means 450 and 460. Specifically, a preferred embodiment for such closing means 450 and 460 is Velcro®, wherein closing means 450 is hook section and closing means 460 is receiver section. Pressure inflatable cuff 430 is located adjacent the open end of application bag 410. Pressure pump 480 inflates pressure inflatable cuff 430 through tube 490. Pressure pump 480 can be manually or mechanically inflated. Pressure inflatable cuff 430 when inflated creates a seal sufficient to prevent the antiseptic from escaping application bag 400.

Figure 5:
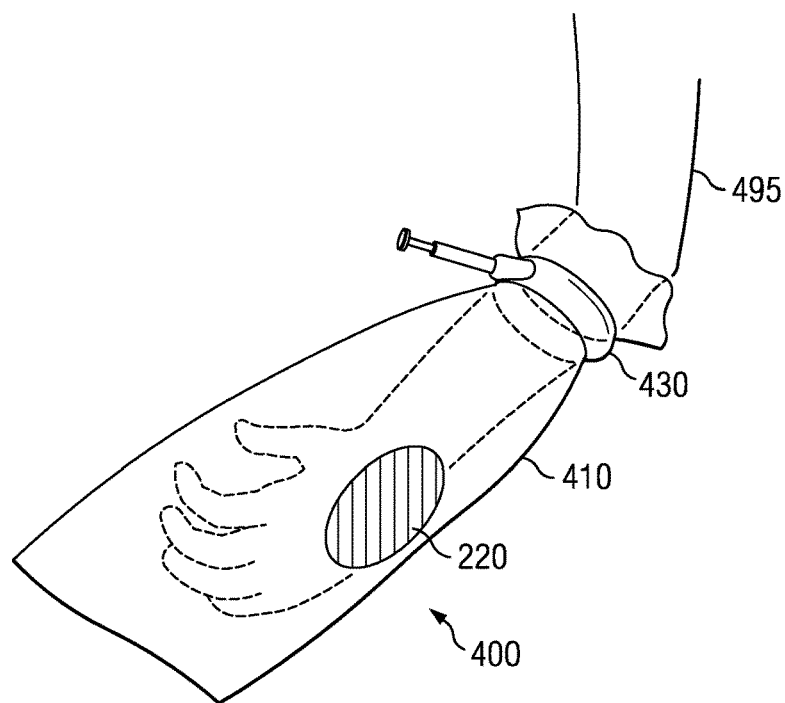
FIG. 5 is a perspective view of a preferred embodiment of the invention disclosed.

FIG. 5 illustrates solution applicator 400 when pressure inflatable cuff is inflated.

Figure 6:
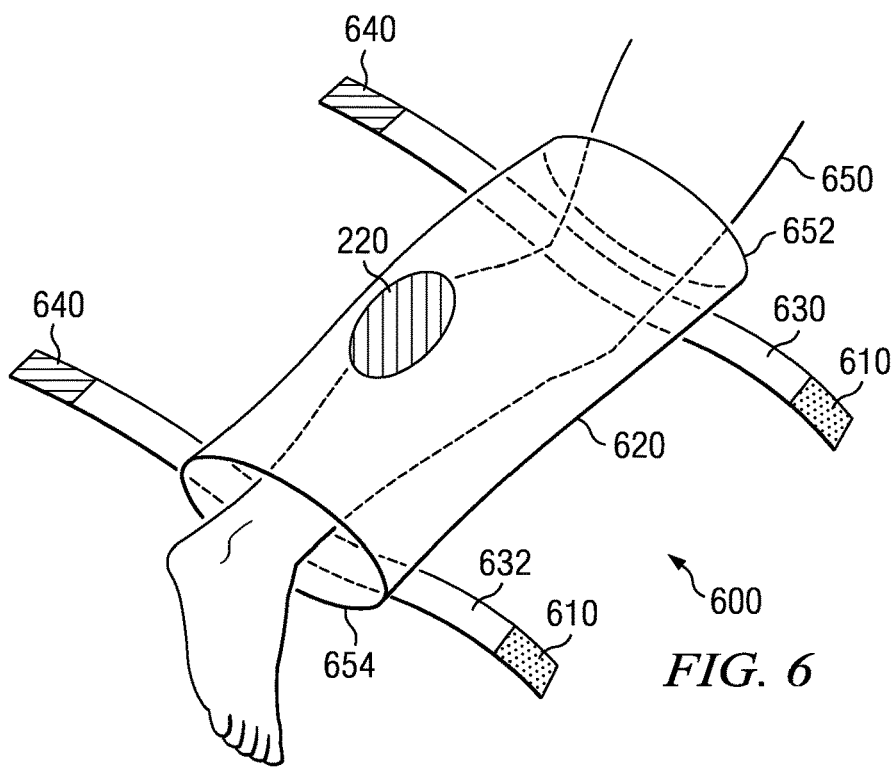
FIG. 6 is a perspective view of a preferred embodiment of the invention showing the use of two closing means.

FIG. 6 shows yet another preferred embodiment of solution applicator 600. This embodiment can be employed when only a section of a patient's appendage 650 is to be treated with antiseptic. In this embodiment, application bag 620 is open at both ends 652 and 654 and is tubular. The length of application bag 620 can vary depending on the size of the area being treated.

Each end of application bag 620 is closed around patient's appendage 650 by use of closing means 630 and 632. Each closing means is similar to those embodiments already described. For example, if Velcro® is used to secure closing means 630 and 632, Velcro® closure includes hook sections 640 and receiver sections 610 as necessary to use the closing means 630 and 632 as described. Solution deployment pouch 220 is adhered to the inside of application bag 620 between the closing means on either end.

Figure 7:
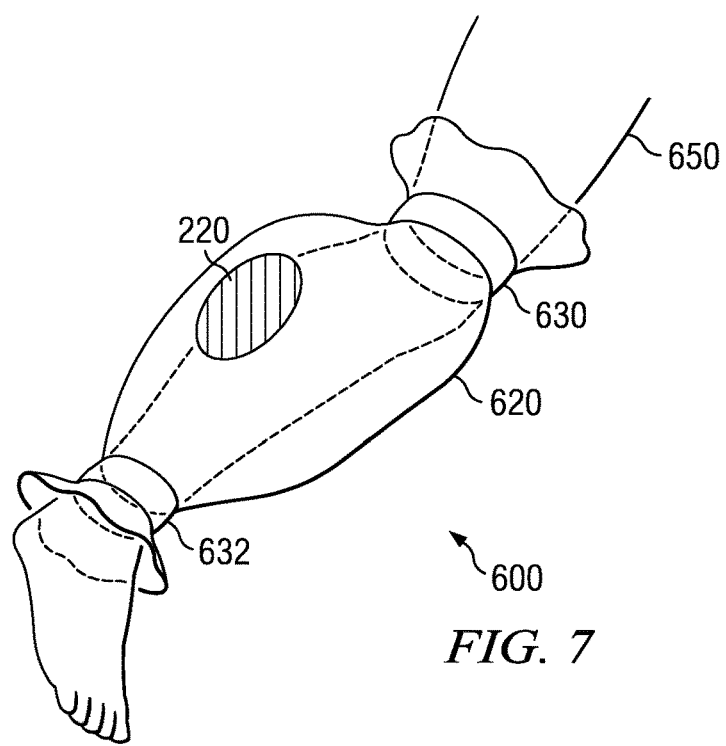
FIG. 7 is a perspective view of a preferred embodiment of the invention showing two closing means.

FIG. 7 illustrates solution applicator 600 after each end of application bag 620 has been closed around patient's appendage 650. The portion of application bag 620 between closing means is loose-fitting around patient's appendage 650. Solution deployment pouch 220 is ruptured and antiseptic fluid escapes to be massaged into the skin. All excess antiseptic is retained in the application bag 620 until closing means 630 and 632 are released and application bag 620 is removed.

Figure 8:
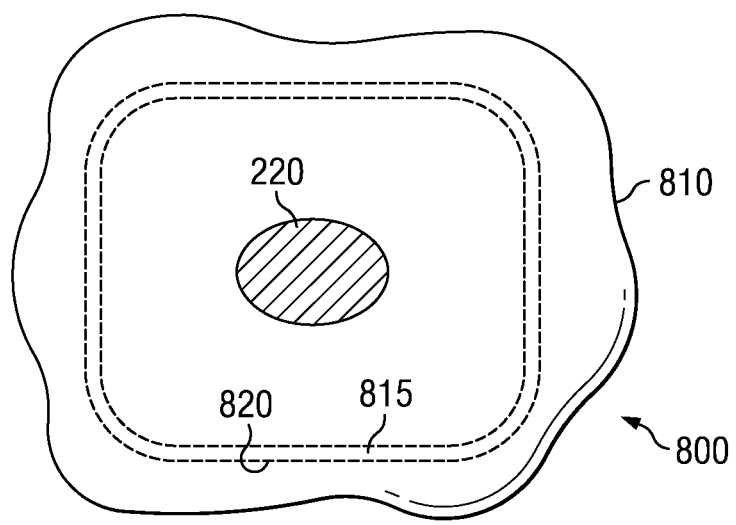
FIG. 8 is a plane view a preferred embodiment of the invention.

FIG. 8 shows a preferred embodiment of solution applicator 800. Solution applicator 800 can be used to apply antiseptic to a relatively flat area of the body, such as the abdomen or back. Application bag 810 forms a generally hemispherical shape placed over the surgical site. In the preferred embodiment, application bag 810 allows a clearance of about 3 inches when attached to the patient.

The circumference of application bag 810 is lined with a disk-like adhesive strip 815. The adhesive strip is of sufficient tackiness to adhere to form a seal with the patient's skin, but still removable without injury. Suitable adhesives are well known in the art. The width of the adhesive strip should range between ¼ inch and 1 inch. In the preferred embodiment, a removable waxed tape covers the adhesive strip until such time as solution applicator will be applied to patient. Attached to the interior of application bag 810 is solution deployment pouch 220 which contains antiseptic for treatment of the patient. Deployment and use of the antiseptic fluid is similar to that described above.

Figure 9:
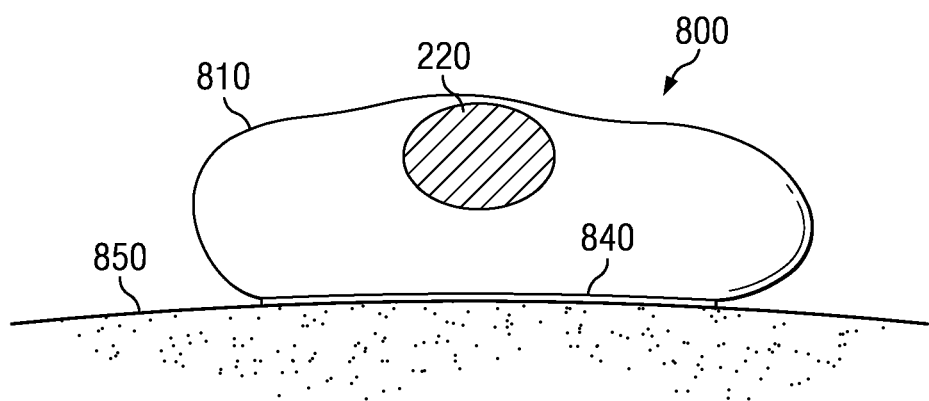
FIG. 9 is a side view of a preferred embodiment of the invention.

FIG. 9 illustrates a side view of solution applicator 800 attached to abdomen of patient 850. After adhesive strip 840 is applied to the skin of the patient, the remainder of application bag 810 allows for user to maneuver application bag 810 to rub or massage the antiseptic fluid over the skin without removing adhesive strip 840 from the skin.

Referring to FIGS. 10A, 10B, 10C, and 10D, application bag 910 has outside surface 914 and inside surface 915. Application bag 910 further has a plurality of holes 911, 912, and 913, to accommodate the attachment of a plurality of scrub brushes 900. Hole 911 is located generally at the anterior knee area. Holes 912 and 913 are located on opposite sides of the ankle area. Scrub brush 900 is attached to inside surface 915 by an adhesive or welding means known in the art. Handle 902 then protrudes through the holes 911, 912, and 913, extending past outside surface 914 to allow a user to move scrub brush 900 to scrub the patient's skin without the user making contact with the patent's skin.

Figure 10A:
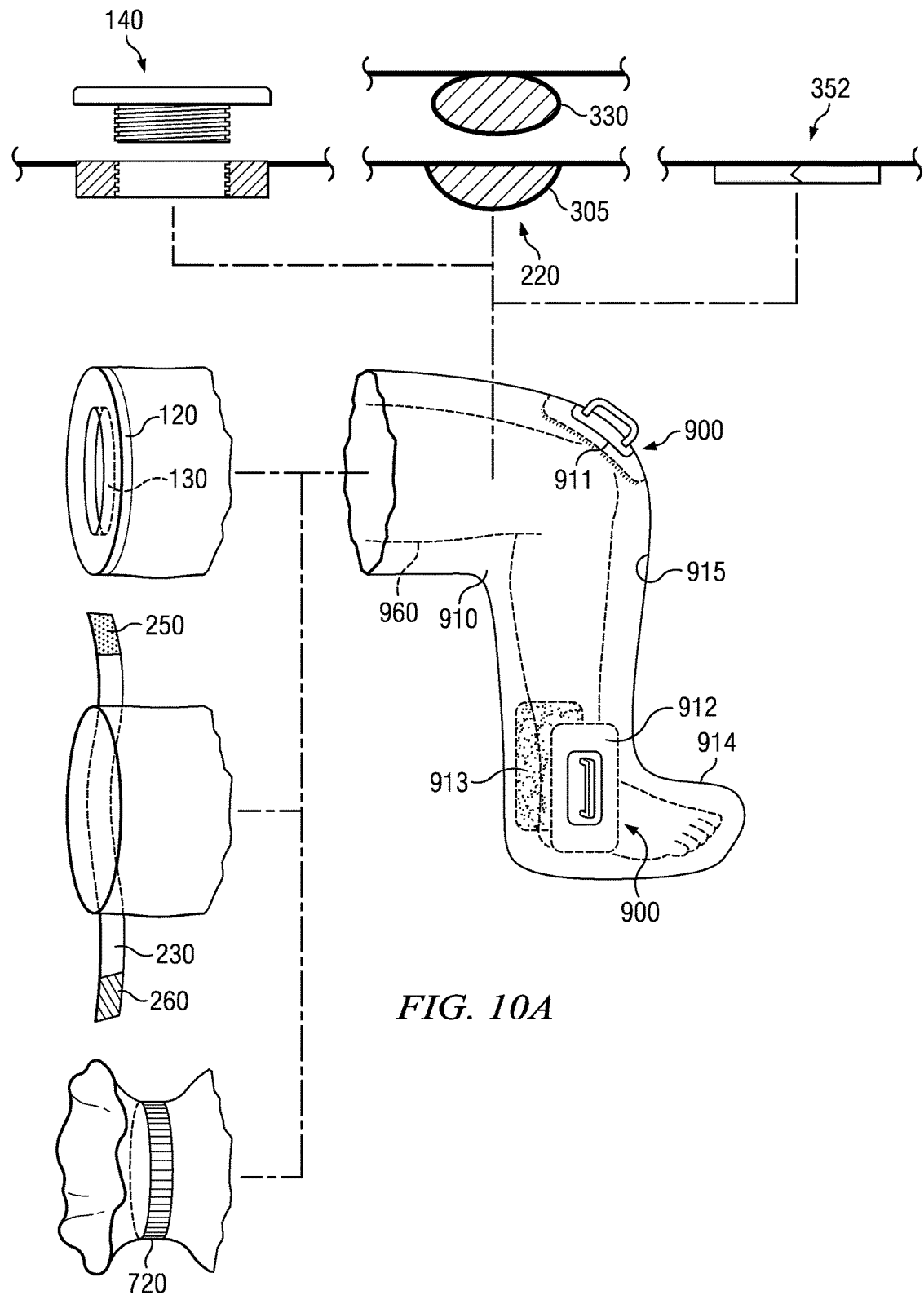
FIG. 10A is a side view of a preferred embodiment.
Figure 10B:
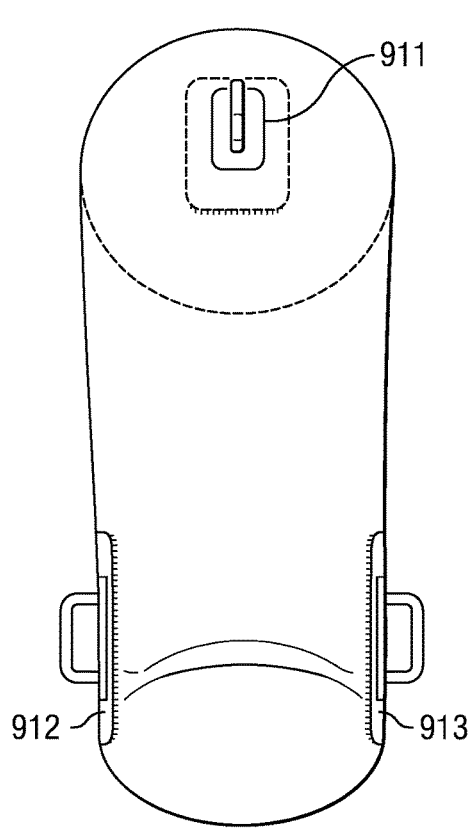
FIG. 10B is an end view of a preferred embodiment.
Figure 10D:
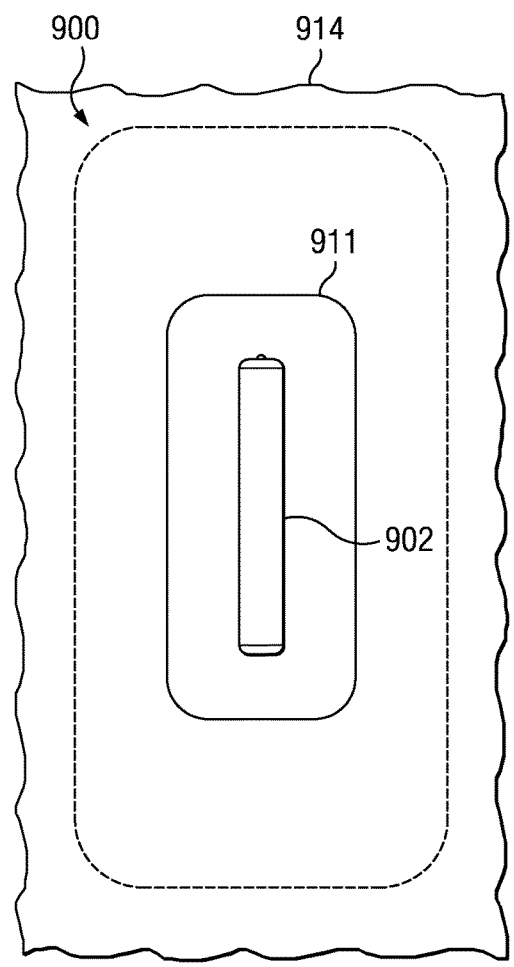
FIG. 10D is a detail top view of a preferred embodiment.
Figure 10C:
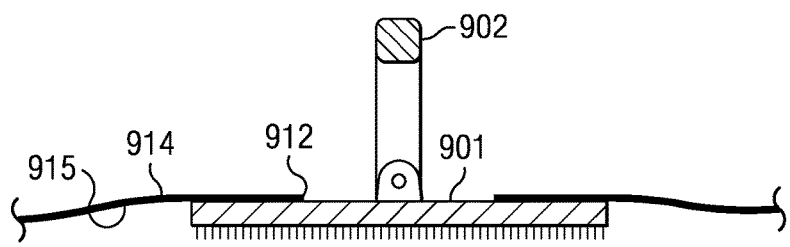
FIG. 10C is a partial section view of a preferred embodiment.
Figure 11A:
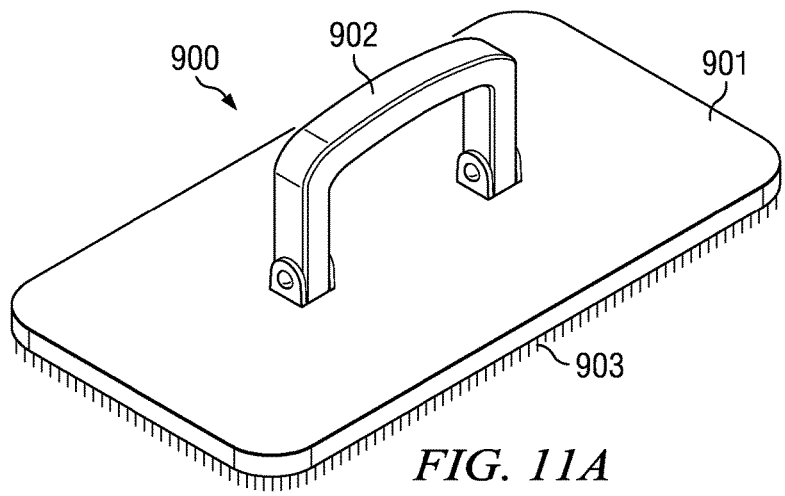
FIG. 11A is a perspective view of a scrub brush of a preferred embodiment of the invention.
Figure 11B:
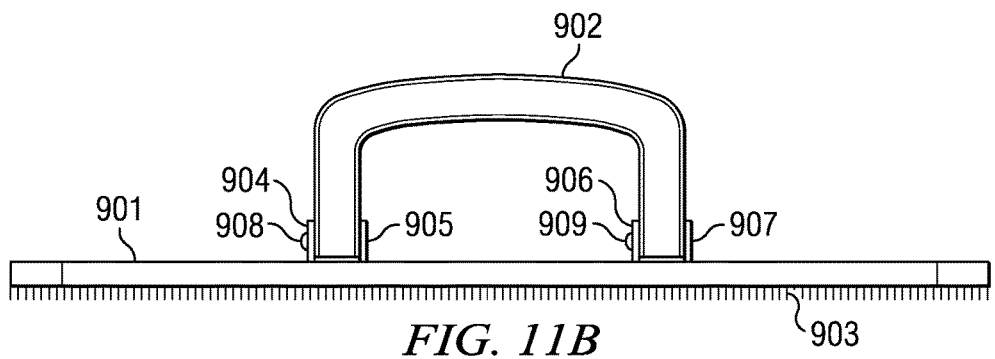
FIG. 11B is a side view of a scrub brush of a preferred embodiment of the invention.
Figure 11C:
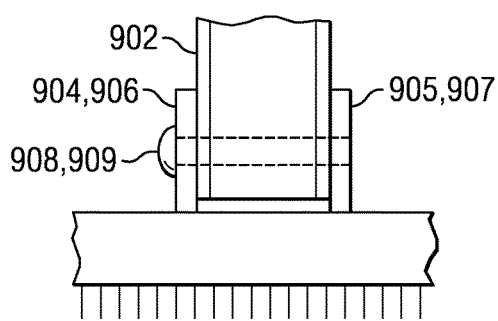
FIG. 11C is a detail view of a connection means of a scrub brush of a preferred embodiment of the invention.
Figure 11D:
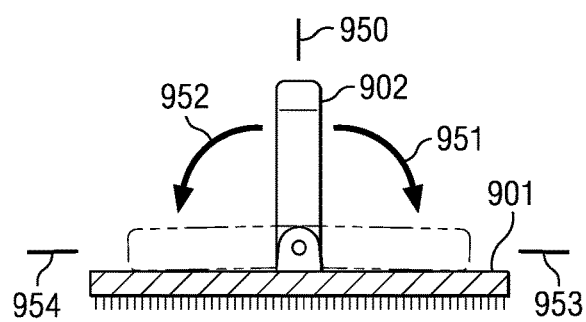
FIG. 11D is an end view of a scrub brush of a preferred embodiment of the invention.

Referring to FIG. 10A, application bag 910 can include a multitude of sealing means including one of, but not limited to, the aforementioned gasket 120 with hole 130, closing means 230 with hook section 260 and receiver section 250, and elastic band 720.

Application bag 910 can include a multitude of antiseptic insertion means including one of, but not limited to, the aforementioned fill/drain port 140, solution pouch 220 including cavity 305 and capsule 330, and plastic rectangle 352.

In a preferred embodiment, application bag 910 is shaped to generally match leg 960. In this embodiment, scrub brushes 900 are attached to application bag 910 at the anterior knee area and opposite sides of the ankle. However, those skilled in the art will appreciate that application bag 910 can be made in a multitude of shapes to generally match other extremities or adapted to fit a torso and scrub brushes 900 can be attached to application bag 910 at any desired location.

In a preferred embodiment, application bag 910 is made of HDPE (high density polyethylene) which is typically translucent, but not fully transparent. In other embodiments, the application bag can be made out of LDPE (low density polyethylene) and can be quite clear, but still not totally transparent. In other embodiments, LLDP (linear low density polyethylene) can be employed where a higher structural rigidity is required by the cleaning process. Other flexible sheeting can be used so long as it is inert with respect to the antiseptic solution. Other plastics can be used if complete transparency is required for various cleaning processes. In other embodiments, the application bag can be color coded to indicate different sizes, different antiseptics contained within the bag or the proper operating theater for the patient.

In another preferred embodiment, the interior and/or exterior of application bag 910 can be textured to increase the effectiveness of the application of the antiseptic to the patient. If on the exterior of the application bag, the purpose of the texturing is to increase friction between the hands of the user and the exterior of the application bag to aid in manipulation of the application bag during use. If on the interior of the application bag, the textured surface is useful in scrubbing the surgical site to remove bacterial colonies by applying an increased friction to the surgical site. In one embodiment, the textured surface may be used to scrub the surgical site and/or an area out of the reach of scrub brush 900. In one embodiment, the textured surface and, the surgical site or the out-of-reach area, has a higher friction coefficient than the interior surface and, the surgical site or the out-of-reach area. In one embodiment, the textured surface and the hands of the user has a higher friction coefficient than the exterior surface and the hands of the user. The harder the surgical site and/or the out-of-reach area is scrubbed with the textured surface, the higher the friction applied to the surgical site and/or the out-of-reach and vice versa. Examples of textures can include a set of raised ribs, chevron patterns, diamond patterns or random "crinkling" having a varying thickness. Any raised pattern that extends from the interior or outside surface may be employed. Other plastics can be used if complete transparency is required for various cleaning processes. In other embodiments, the application bag can be color coded to indicate different sizes, different antiseptics contained within the bag or the proper operating theater for the patient.

In a preferred embodiment, application bag 910 can be formed from two identical or nearly-identical sized sheets. Both sheets will have the same or nearly the same shape. All of the sides but one are sealed or fused by an adhesive or heat welding as known in the art, leaving the remaining side open. The flat format of the completed application bag increases the ease of storage and/or deployment of the bag from a cardboard box as known in the art. The shape also promotes economy of manufacture.

In another preferred embodiment, application bag 910 can be formed by a flexible tubular extrusion of plastic. After manufacture, the tube can then be cut to shape. After being cut, ends are sealed or fused by known inductive welding means leaving one end open.

In a preferred embodiment, the general circumference of application bag 910 is at least 2 inches larger than the part of the body being decontaminated. The width of application bag 910 in a preferred embodiment is usually between 2 inches and 40 inches. In the preferred embodiment, the general length of the application bag is at least 2 inches longer than the part of the body being placed in application bag 910. The length of application bag 910 in a preferred embodiment would be between 2 inches and 60 inches. Application bag 910 should also allow for complete articulation of any joint surrounded in order to allow for complete coverage by the antiseptic solution.

Referring to FIGS. 11A, 11B, 11C, and 11D, a preferred embodiment of scrub brush 900 comprises brush 901, and rotatable handle 902. Brush 901 includes bristles 903, which are attached to brush 901. Handle 902 is connected to brush 901 at connection brackets 904, 905, 906, and 907. Pins 908 and 909 are inserted into connection bracket 904 and 906 sliding through handle 902 into connection brackets 905 and 907.

Handle 902 can rotate about an axis adjacent to brush 901. Handle 902 can be moved from position 950, which is generally perpendicular to brush 901. Handle 902 can be moved in either direction 951 to rest on brush 901 at position 953, which is adjacent to brush 901. Alternatively, brush 902 can be moved in direction 952 to position 954, which is adjacent to brush 901.

In a preferred embodiment, brush 901 and handle 902 are constructed of a transparent plastic. Bristles 903 are also constructed of a flexible plastic. It will be appreciated by those skilled in the art that a multitude of transparent and durable materials may be substituted for the construction of scrub brush 900 so long as it is inert with respect to the antiseptic solution.

In a preferred embodiment, scrub brush 900 is attached to application bag 910 in each of holes 911, 912 and 913 with an adhesive or welding means known in the art. The adhesive is applied to form a seal around each scrub brush and each hole.

In use, application bag 910 including an antiseptic insertion means is raised to a temperature approximately equal to that of the patient. An indication of the proper temperature is shown by the color of the plastic rectangle included on the deployment pouch. The application bag is extended and placed around the surgical site. In a preferred embodiment, application bag 910 is secured around the proximal end of the extremity. The distal end of the extremity resides in the interior of the application bag.

The antiseptic is introduced into application bag 910 through antiseptic insertion means 140, 220, or 352. The exterior of the application bag is then manipulated to assure coverage of the appendage by the antiseptic fluid. The antiseptic fluid is then rubbed or massaged into the skin through application bag 910 to dislodge biological communities. Scrub brush 900 and/or application bag 910 is manipulated to scrub the skin to dislodge bacterial colonies. Excess antiseptic fluid is retained by application bag 910. Since application bag 910 is transparent or substantially transparent, a visual examination of the extremity is conducted to assure that adequate and complete coverage of the surgical site has been made.

Upon removal of application bag 910, care must be taken to ensure that any portion of the non-sterile exterior of application bag 910 does not come into contact with the now sterile extremity of the patient. To accomplish removal without contact, gasket 120, closing means 230, or elastic band 720 is rolled back so that only its sterile interior is adjacent the extremity. Application bag 910 is then removed by sliding it off of the extremity, making sure that the rolled back edge is the only point of contact.

Figure 12A:
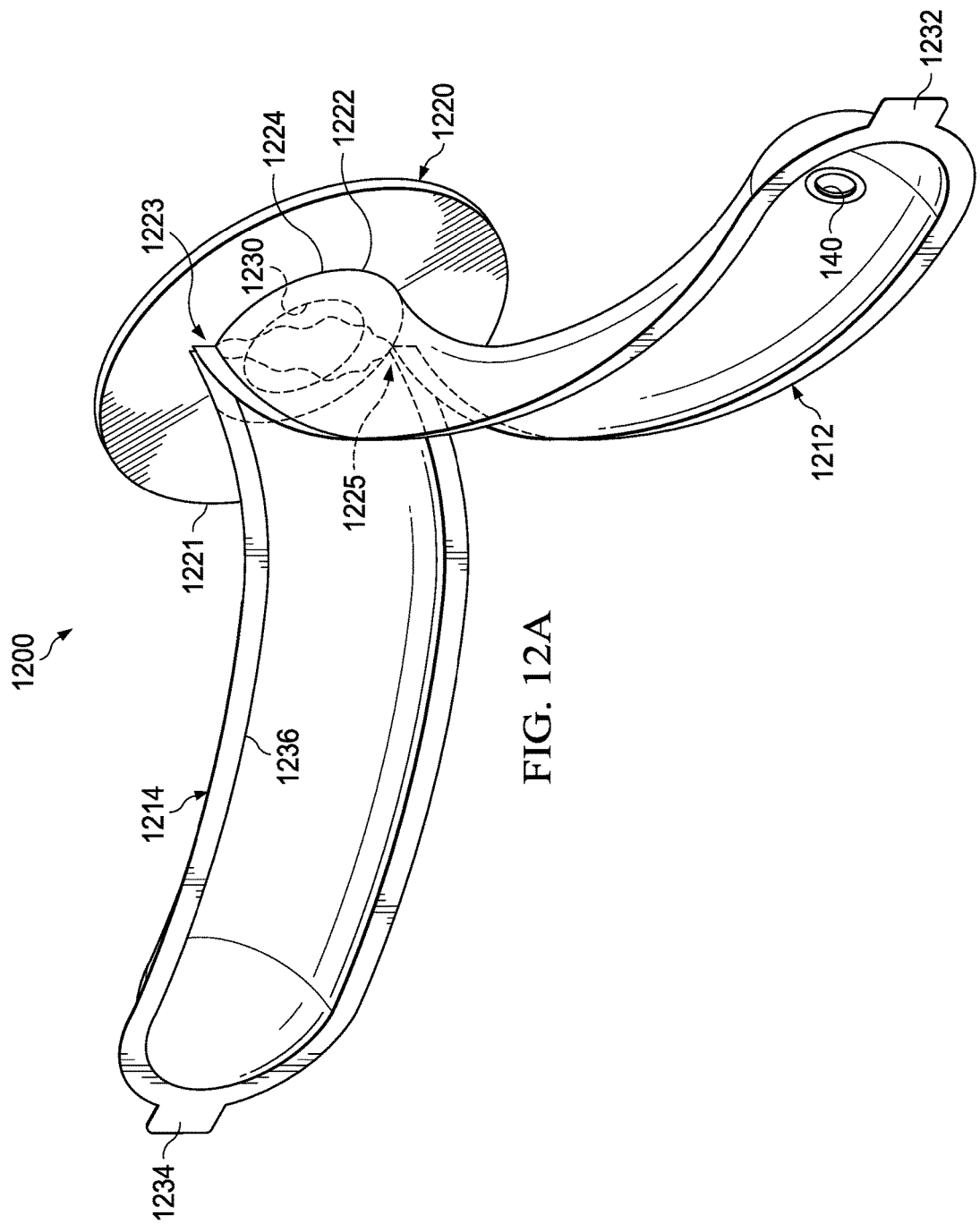
FIG. 12A is a perspective view of a preferred embodiment showing two resealable halves separated.
Figure 12B:
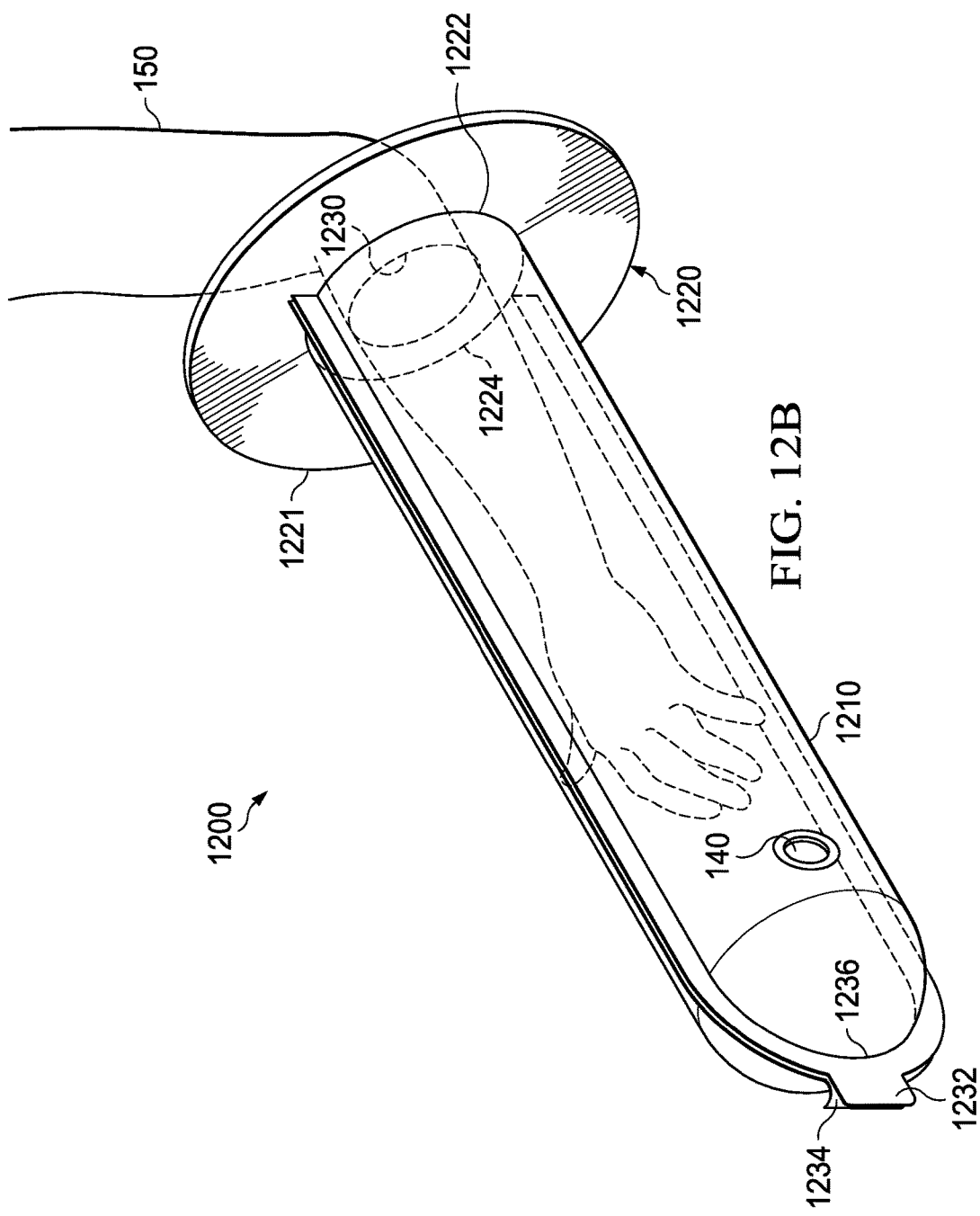
FIG. 12B is a perspective view of a preferred embodiment showing two resealable halves joined.

FIGS. 12A and 12B show a preferred embodiment of solution applicator 1200. Solution applicator 1200 comprises two releasably joinable halves connected to a flexible gasket.

Referring to FIGS. 12A and 12B, application bag 1210 is comprised of first portion 1212 and second portion 1214. First portion 1212 and second portion 1214 may be equally sized, separate halves or first portion 1212 and second portion 1214 may be formed from a single sheet folded on one edge. An end of first portion 1212 and an end of second portion 1214 are each fused or sealed to gasket 1220 through a known adhesive, tape, or heat welding to ensure a sealed attachment. First portion 1212 is attached to gasket 1220 at attachment area 1222 and second portion 1214 is attached to gasket 1220 at attachment area 1224. The shape of the attachment areas are generally semicircular, but other shapes are possible. Attachment areas 1222 and 1224 converge at points 1223 and 1225 thus a complete seal to gasket 1220 is achieved. First portion 1212 includes tab 1232 and second portion 1214 includes tab 1234.

Gasket 1220 can be manufactured from synthetic rubber, such as neoprene or nitrile, or a resilient plastic polymer. The gasket color can be coded to indicate the size and/or shape of the bag making for easy and error free deployment of the antiseptic solution.

Gasket 1220 is generally flat and circular shaped, however oval and polygonal shapes would suffice. Gasket 1220 has edge 1221 along the perimeter of gasket 1220 and hole 1230 in the relative center of gasket 1220. In a preferred embodiment, diameter of hole 1230 ranges between about 1 inch and 15 inches. However, those skilled in the art will recognize that other sizes can be provided to accommodate different patients and circumstances. Hole 1230 should fit around a body extremity such as to prevent the antiseptic solution from escaping application bag 1210 when in use. Attachment areas 1222 and 1224 are located between hole 1230 and perimeter 1221.

Attached to first portion 1212, second portion 1214, or both is fastening means 1236. Fastening means 1236 releasably attaches first portion 1212 to second portion 1214 to form application bag 1210. Fastening means 1236 can be any releasable fastening means that is "watertight" such that the antiseptic introduced into application bag 1210 remains inside application bag 1210 when the first portion is fastened to the second portion. Fastening means 1236 can include, but is not limited to, releasable adhesive or a plastic zipper similar to Ziplock®.

Application bag 1210 can include a multitude of antiseptic insertion means including one of, but not limited to, the aforementioned fill/drain port 140, solution pouch 220 including cavity 305 and capsule 330, and plastic rectangle 352. Additionally, instead of gasket 1220, application bag 1210 may incorporate elastic band 720 or closing means 230 with hook section 260 and receiver section 250. The interior and/or exterior surfaces of application bag 1210 may be textured and/or include a brush or other high friction scrubber.

Figure 13:
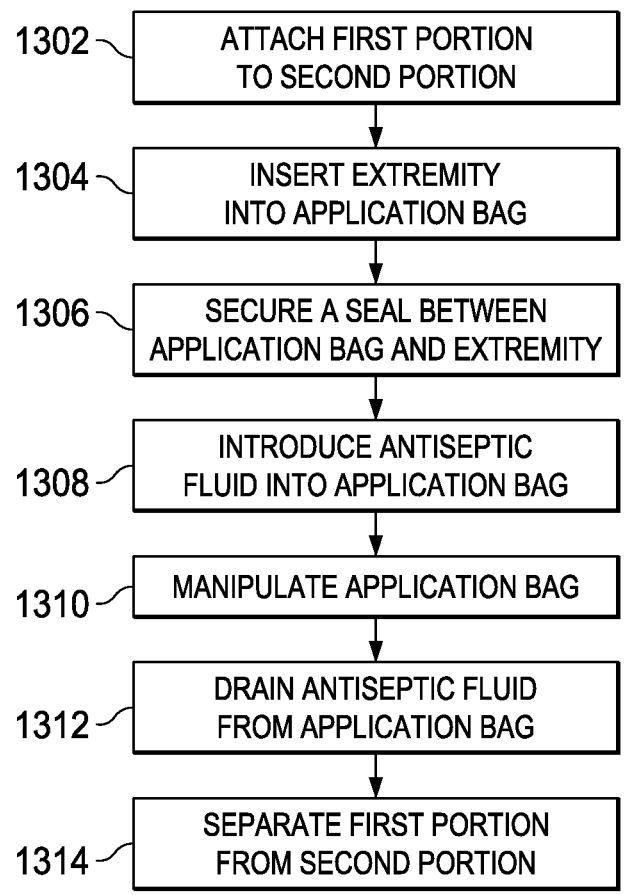
FIG. 13 is a flow chart of steps involved in the use of a preferred embodiment.

Referring now to FIG. 13, the steps for use of application bag 1210 are shown. At step 1302, first portion 1212 is joined to second portion 1214 with fastening means 1236. Fastening means 1236 provides a watertight seal. At step 1304, appendage 150 is inserted into application bag 1210 through hole 1230 in gasket 1220. Appendage may be inserted through hole 1230 after fastening first portion 1212 to second portion 1214 or first portion 1212 may be fastened to second portion 1214 after appendage 150 passes through hole 1230. At step 1306, gasket 1220 secures a seal between application bag 1210 and appendage 150.

Once first portion 1212 is fastened to second portion 1214, at step 1308, antiseptic fluid is introduced to the interior of application bag 1210 through antiseptic insertion means 140, 220, or 352. At step 1310, application bag 1210 is manipulated to apply the antiseptic fluid to the appendage and to dislodge bacterial colonies.

After sterilizing the appendage with the antiseptic fluid, at step 1312, the excess antiseptic fluid is drained through fill/drain port 140 or by separating the first portion from the second portion without disturbing the appendage. At step 1314, if not previously separated, first portion 1212 is separated from second portion 1214. To separate the first portion from the second portion, tab 1232 is peeled away from tab 1234 such that first portion 1212 is unfastened from second portion 1214. With the appendage sterilized and exposed, gasket 1220 may remain in place while physicians move forward with surgery on the appendage. Post surgery, application bag 1210 may be reassembled to protect the surgical site from bacteria before transferring the patient from the surgical environment to the recovery area.

Those skilled in the art will recognize that a more complete application of antiseptic fluid can be made due to the fact that application takes place outside the operating theater. Those skilled in the art will also recognize that the antiseptic can be retained on the surgical area longer, promoting a more thorough decontamination. Those skilled in the art will also recognize that since the decontamination can take place outside the operating theater that substantial operating theater time can be saved with resulting monetary savings to the patient and the hospital.

A bacterial load comparison of standard operating room sterilization techniques versus use of a surgical preparation solution applicator bag for preparing a patient's skin for surgery prior to entering the surgical theater as disclosed herein was performed A summary of the results are presented here.

The bacterial load comparison utilized a standard skin-swabbing followed by inoculation and agar plating approach to quantify the bacterial load before and after sterilization. In total, 60 skin-swab samples were collected for processing and 27 were used for final analysis.

For collection of swabbing, a single person served as their own control. Per person, left and right arms were swabbed individually and collected in tubes. Then one arm was sterilized with standard operating room sterilization techniques while the other arm was sterilized using the disclosed surgical preparation solution applicator bag. Both arms were then individually swabbed again and collected in individual tubes resulting in four samples per person.

Samples were plated without dilution on three Petri dishes containing Brain-heart infusion agar (Difco) supplemented by defibrinated horse blood (BAP-medium), thus providing a triplicate count per sample. The plates were incubated at 30° C. and the resulting colonies were counted at 48 hours and 72 hours post-platting. This specific Petri dish medium was selected because it supports the growth of most common skin bacteria and particularly those bacteria that can cause wound infections (e.g., enterics, *Staphylococcus* and *Streptococcus* spp., *Pseudomonas aeruginosa*).

Following colony counting, six samples were removed from further consideration due to spreading fungal growth. The presence of fungi on the Petri dishes does not necessarily indicate contamination from sampling or plating. Fungi may have been present on the skin of sampled individuals. The medium used in the study was designed for counting bacteria, specifically because (1) bacterial count was the focus of the study and (2) bacteria are expected to be the main component of skin microflora. Moreover, counting of fungal colonies was not possible due the exceedingly fast growth rate of fungal colonies on medium. The study did not attempt to quantify fungal load and accordingly samples displaying fungal growth were excluded from the study.

Other samples contained no bacterial growth or on average less than one bacterium per Petri dish replicate. For these samples, both left and right arms and three replicates from each arm produced identical numbers (i.e., a lack of bacterial growth) suggesting that a lack of bacteria is not associated with sampling or plating errors but rather the lack of a culturable bacterial load on the skin of these subjects.

Additional samples yielded one or more Petri dishes with confluent colonies and were assigned with "Too numerous to count" designation. The number of plated bacteria for these samples exceeded 1,000 which is considered an upper limit of colonies that can be counted on one standard Petri dish. Accordingly, the twenty seven remaining samples with two to three replicates each were selected for further statistical analyses.

Qualitatively, both sterilization techniques performed superbly by removing almost all bacteria in the samples. For the standard technique, an average number of colonies recovered was 0.05 per plate. For the surgical preparation solution applicator bag disclosed herein, the average number of colonies recovered was 0.012 colonies per plate. A paired t-test was used to compare the number of colonies grown in a Petri dish from samples collected after the sterilant treatment of an individual to the number of colonies grown in a control Petri dish from the same individual.

The resulting $t(78 \text{ degrees of freedom})=1.778172$ and $p=0.039636$. Thus, the result is significant at $p \leq 0.05$. When $p<0.05$, "the magnitude of the effect" becomes of interest. The observed mean difference of $8.67 \pm 4.88$ suggests that on average the disclosed surgical preparation solution applicator bag killed 8.67 more bacteria/per plate in this study than the standard sterilization techniques. Although, the mean difference can be explained by a systematic sampling error, the paired t-test demonstrates that the surgical preparation solution applicator bag disclosed herein is at least as good as the standard sterilization techniques commonly used in the operating theater.

In summary, the surgical preparation solution applicator bag disclosed herein demonstrated the efficiency of sterilization not worse than and possibly better than that of standard techniques, essentially killing all bacteria on sampled skin areas.

The embodiments have been described in detail with particular reference to certain preferred embodiments thereof, but it will be understood that variations and modifications can be effected within the scope of the embodiments, especially to those skilled in the art.

The invention claimed is:

1. A containment device for deploying an antiseptic preparation to an extremity of a patient comprising:
   a flexible container, comprised of a first portion and a second portion, configured to surround the extremity;
   a fastening means, for the separable and resealable attachment of the first portion to the second portion, attached to the flexible container;
   a sealing means, fused to the flexible container, capable of securing a seal between the extremity and an exterior of the flexible container;
   a sealable opening in the flexible container for introduction of the antiseptic preparation; and, whereby the antiseptic preparation is deployed into and contained within the flexible container.

2. The containment device of claim 1, wherein the fastening means is one from the group consisting of an adhesive and a zipper.

3. The containment device of claim 1, wherein a set of textures are formed on an interior surface of the flexible container.

4. The containment device of claim 1, wherein the flexible container further comprises at least one high friction scrubber attached to an interior surface of the flexible container.

5. The containment device of claim 1, wherein the sealing means comprises:
a flexible gasket having a perimeter and a hole within the perimeter;
wherein the first portion and the second portion are attached to the flexible gasket between the perimeter and the hole.

6. The containment device of claim 5, wherein the flexible gasket is color-coded to indicate a size of the flexible container.

7. The containment device of claim 1, wherein the flexible container is color-coded to indicate a relationship between the patient and an operating theater.

8. A device for applying an antiseptic to an extremity comprising:
a manipulatable membrane, comprised of a first portion releasably and resealably fastened to a second portion;
a flexible seal fixed to the membrane;
an antiseptic deployment pouch in the membrane; and,
whereby the antiseptic is deployably introduced inside the membrane and contained inside the membrane and removes contaminants from the extremity.

9. The device of claim 8, wherein the antiseptic deployment pouch comprises a solution pouch and one or more of a cavity in the manipulatable membrane, and a breakable release portal.

10. The device of claim 8, wherein the first portion is fastened to the second portion by at least one of an adhesive and a zipper.

11. The device of claim 8, further comprising an antiseptic temperature indicator in heat conductive contact with the antiseptic to be applied.

12. The device of claim 8, wherein the flexible seal is one from the group of a flexible gasket, an elastic band, and a fabric hook-and-loop fastening band.

13. The device of claim 8, wherein an interior surface of the membrane includes at least one from the group of a textured surface and a brush.

14. A containment device for deploying an antiseptic preparation to an extremity of a patient, comprising:
a flexible container, comprised of a first portion and a second portion, configured to surround the extremity;
a fastening means, for the separable and resealable attachment of the first portion to the second portion, attached to the flexible container;
a sealing means, attached to the flexible container, capable of securing a seal between the extremity and an exterior of the flexible container;
a sealable opening in the flexible container for introduction of the antiseptic preparation;
whereby the antiseptic preparation is deployed into and contained within the flexible container;
wherein the flexible container further comprises at least one high friction scrubber attached to an interior surface of the flexible container;
wherein the at least one high friction scrubber comprises a brush, having a plurality of bristles; and,
wherein a handle is connected to the brush.

15. A containment device for deploying an antiseptic preparation to an extremity of a patient, comprising:
a flexible container, comprised of a first portion and a second portion, configured to surround the extremity;
a fastening means, for the separable and resealable attachment of the first portion to the second portion, attached to the flexible container;
a sealing means, attached to the flexible container, capable of securing a seal between the extremity and an exterior of the flexible container;
a sealable opening in the flexible container for introduction of the antiseptic preparation;
whereby the antiseptic preparation is deployed into and contained within the flexible container; and,
wherein the sealable opening is a semi rigid ring sealed by a matching and removable plug.

16. A device for applying an antiseptic to an extremity, comprising:
a manipulatable membrane, comprised of a first portion releasably and resealably fastened to a second portion;
a flexible seal attached to the membrane;
an antiseptic insertion means in the membrane;
whereby the antiseptic is introduced into and contained inside the membrane and removes contaminants from the extremity; and,
wherein the antiseptic insertion means includes an opening and a cap securable within the opening forming a resealable port.

17. In a device for the surgical preparation of an extremity of a patient comprising a flexible container comprised of a first portion releasably attached to a second portion, a gasket attached to the flexible container, and at least one of an antiseptic deployment pouch, capsule, and cavity cover in the flexible container, a method comprising the steps of:
attaching the first portion to the second portion;
inserting the extremity into the flexible container;
securing a seal between the flexible container and the extremity with the gasket;
introducing an antiseptic fluid with the at least one of the antiseptic deployment pouch, capsule, and cavity cover;
dispensing the antiseptic fluid by manipulating an outside surface of the flexible container; and,
manipulating the flexible container to apply the antiseptic fluid to the extremity.

18. The method of claim 17, further comprising:
draining the antiseptic fluid from the flexible container; and,
separating the first portion from the second portion.

19. In a device for the surgical preparation of an extremity of a patient comprising a flexible container comprised of a first portion releasably attached to a second portion, a gasket attached to the flexible container, and an antiseptic introduction means in the flexible container, a method comprising the steps of:
attaching the first portion to the second portion;
inserting the extremity into the flexible container;
securing a seal between the flexible container and the extremity with the gasket introducing an antiseptic fluid with the antiseptic introduction means;
manipulating the flexible container to apply the antiseptic fluid to the extremity;

providing a friction surface attached to an interior surface of the flexible container; and, manually scrubbing the extremity with the friction surface to remove bacterial colonies.

* * * * *